United States Patent [19]

Anderson

[11] 4,192,866

[45] Mar. 11, 1980

[54] ANORECTAL MEDICATION

[76] Inventor: Ralph Anderson, 6218 Freeman, Kansas City, Kans. 66104

[21] Appl. No.: 949,819

[22] Filed: Oct. 10, 1978

[51] Int. Cl.$^2$ .................... A61K 33/06; A61K 33/04; A61K 35/78

[52] U.S. Cl. .................... 424/154; 424/165; 424/195; 424/196

[58] Field of Search ............... 424/196, 165, 195, 154

[56] References Cited

U.S. PATENT DOCUMENTS

| | | | |
|---|---|---|---|
| 3,417 | 1/1844 | Riley | 424/165 |
| 55,474 | 6/1866 | Eisenhut | 424/165 |
| 73,135 | 1/1868 | Taylor | 424/165 |
| 122,608 | 1/1872 | Heins | 424/196 |
| 141,961 | 1/1873 | Steenberger | 424/165 |
| 199,684 | 1/1878 | Beattie | 424/196 |
| 224,031 | 2/1880 | Myers | 424/196 |
| 284,314 | 9/1883 | Lucas | 424/196 |
| 377,979 | 2/1888 | Banks | 424/196 |
| 3,542,921 | 11/1970 | Myatt | 424/196 |

FOREIGN PATENT DOCUMENTS

| | | | |
|---|---|---|---|
| 1291 | of 1894 | United Kingdom | 424/196 |
| 962226 | 7/1964 | United Kingdom | 424/196 |

OTHER PUBLICATIONS

Steinmetz, Codex Vegetabilis (1957), p. 1066 t/m 1075, entry 1074.

*Primary Examiner*—Donald B. Moyer
*Attorney, Agent, or Firm*—Fishburn, Gold & Litman

[57] ABSTRACT

A preparation for the treatment of anorectal diseases, especially hemorrhoids, comprising polyglycerides and ripe berry products of the plant *Solanum carolinense* (Horse Nettle). In a particular composition of the medication, a heated mixture is made of the polyglycerides and fragmented *Solanum carolinense* berries. In a preferred composition, subliminated sulfur, ammonium alum, and turpentine are added to the mixture which is agitated and filtered, thereby producing a substantially homogenous medication.

3 Claims, No Drawings

ANORECTAL MEDICATION

BACKGROUND OF THE INVENTION

This invention relates to a medication for the treatment of anorectal disease or irritations, and in particular to a medication employing the ripe berries of the plant *Solanum carolinense* as an active healing agent therein.

Various diseases of the anorectal region of the human body are characterized by inflammation, itching, ulcerations and/or lesions with associated pain. By anorectal region as used herein, is meant the anus, the rectum and the lower colon which form the lower portion of the alimentary track in conjunction with the perineum in close proximity to the anal opening. The anorectal region especially means the area in close proximity to the external and internal anal spinctor muscles. The most common of the diseases treated by the medication disclosed herein is hemorrhoids or piles. Several major problems in healing exist in the anorectal region. During bowel evacuation, the fecal mass tends to stretch, tear and irritate the already swollen and inflamed tissue. In addition, because added muscular strain is required during defecation to overcome the swollen tissue around anal spinctor muscles, there is a tendency to cause herniation of the anal walls and further swelling. Also the fecal mass contains numerous infectious organisms which enter damaged tissue and hamper healing. Left untreated, anorectal disease often becomes worse and sometimes requires surgery for removal of hemorroids and/or repair or amputation of a prolapsed anus.

In the prior art treatments, associated with hemorrhoids and other similar diseases, compositions have been developed generally to relieve either the itching (pruritus ani) or the inflammation with varying degrees of success. The efficacy of the prior art treatments in relieving or curing a variety of symptoms is uncertain, as are side effects thereof.

SUMMARY OF THE INVENTION

Therefore, the principal objects of the present invention are: to provide a preparation for use in the anorectal region; to provide such a preparation which shrinks swollen and inflamed tissue; to provide such a preparation which soothes itching; to provide such a preparation which lubricates the fecal mass and softens the tissue to ease defecation; to provide such a preparation which enhances healing of injured tissue and acts as a barrier to infection; to provide such a preparation which can be used in the lower colon to relieve lesions, fissures and other similar problems; to provide such a preparation which has minimal if any unfavorable side effects; to provide a method for the production of such a preparation; and to provide such a preparation which is easy to apply and use, offers relief from pain associated with anorectal disease, heals the area treated in a relatively short time after initiation, and tends to promote permanent relief.

The present invention is an anectoral medication and method for production thereof which employs ripe *Solanum carolinense* berries as an active healing agent in a medium which is normally animal fat or vegetable oil. A preferred embodiment includes subliminated sulfur, ammonium alum, and spirits of turpentine. The preparation is normally applied as an ointment directly to the diseased area in three applications at 24 to 48 hour intervals in amounts of about 5 grams each. The preparation tends to reduce inflammation and swelling, promote healing of fissures, abcesses and lesions, lubricate the region to ease bowel evacuation, soothe itching, and add flexibility to tissue to reduce tearing and irritation in absence of known adverse side effects.

Other objects and advantages of this invention will become apparent from the following description wherein is set forth, by way of example, certain embodiments of this invention.

DETAILED DESCRIPTION OF THE PREFERRED EMBODIMENTS

As required, detailed embodiments of the present invention are disclosed herein, however, it is to be understood that the disclosed embodiments are merely exemplary of the invention which may be embodied in various forms. Therefore, specific details disclosed herein are not to be interpreted as limiting, but merely as a basis for the claims and as a representative basis for teaching one skilled in the art to variously employ the present invention in virtually any suitable application.

In general, the medicinal preparation of the present invention comprises berry products of the plant *Solanum carolinense* dispersed throughout an application medium. The berries for most effective results should be ripe, between green and yellow in color. Dispersal of the active ingredients of the berries (the composition of the active ingredients is uncertain), can be accomplished by slicing, dicing, expressing, mashing or otherwise fragmenting the berries. The berry products dissolved in the medium appear to constitute an active healing element of the present invention.

The application medium should be a viscous liquid or semisolid at body temperature to facilitate use of the preparation. Although the preparation could be used in the form of a semi-solid suppository which melts at body temperature or other suitable application form, an ointment form is preferred because ointments are easier to topically apply directly onto the diseased area, thereby placing healing agents immediately in contact therewith. Polyglycerides, suitable for use in conjunction with human tissue, function well as the medium, in particular animal fats (such as tallow or salt port fat), vegetable oils (such as cottonseed oil, corn oil, soy bean oil, peanut oil, sunflower oil and olive oil) and mixtures thereof provide a suitable medium for the active ingredients of the berries. When triglycerides are used as the medium, they also act as a soothing emollient, providing lubrication and tending to add flexibility to the diseased tissue, so that further tissue damage due to friction or stretching is reduced or eliminated. Besides lubricating and tending to soften the tissue, the triglycerides also appear to form a coating or layer thereon which provides protection from foreign material and acts are a carrier for the active medicinal ingredients while healing occurs.

In a particular embodiment, the preparation according to this invention also contains sulfur, an astringent, and a demulcent. Sulfur in a subliminated state has been found most effective in the preparation. Although the exact effect of the sulfur is uncertain, it is felt to add sulfur for the healing process in the formation of the essential protein amino acid cystine and may act as a catalyst for the other ingredients of the preparation. The astringent may be any suitable tissue contractor such as bismuth subgallate, bismuth subcarbonate, and hamamelis. Preferably the astringent should shrink the tissue and stop bleeding from exposed blood capillaries, but should not further irritate the tissue or be a vascular contractor, so as to reduce needed blood flow to the tissue being healed. Aluminum ammonium sulfate (alum) has been found to perform very well as an astrigent in this service and in conjunction with the other constituents of the preparation. The demulcent soothes and coats the tissue and protects the underlying area from air and irritating agents. There are a number of suitable demulcents, such as glycerine and various oleoresins, however, spirits of turpentine has been found to be preferred in conjunction with the other ingredients described herein. The spirits of turpentine also apparently acts as an emulsifier agent for suspending other active ingredients in a homogenous suspension throughout the preparation. The various ingredients described apparently have a synergistic healing effect when used in conjunction with oneanother.

Thus, a particularly effective embodiment of this invention comprises fragmented berries of *Solanum carolinense*, salt pork fat, subliminated sulfur, aluminum ammonium sulfate, and spirits of turpentine. However, it is envisioned that substitutions for various elements, based upon the above discussion, can be made which will also produce an effective anorectal preparation according to this invention.

In preparing the medication the berries are placed in the application medium and the active ingredients therein are allowed to diffuse into the medium. In order to enhance the diffusion process the berries are fragmented to increase surface area and break the external skin thereof. The medium and berry mixture is also heated above ambient temperature to enhance the diffusion process. For best results, the temperature of the mixture should not be so high as to degrade the medium. Thus the appropriate temperature to use is dependent on the characteristics of the medium and the time available for preparation. As an example, a mixing temperature of about 95° Centigrade (C) has been found suitable when using conventional vegetable oils as a medium. It has also been found that berries sliced in thin layers work well in the invention, although dicing or other methods of fragmatizing will also work.

A method of producing the preparation according to this invention, which is particularly effective, comprises heating triglycerides (either vegetable oil or animal fats) in a container until a preselected temperature is obtained therein, which temperature is related to the particular medium as discussed above. Thinly sliced ripe berries are added to the heated triglyceride forming a mixture which is agitated for about one minute. The liquid is decanted from the berry residue which has turned a crispy brown. Subliminated sulfur is then placed on the surface of the hot, decanted mixture and allowed to remain thereon for about one-half minute, thereafter the sulfur is agitated into the mixture. Aluminum ammonium sulfate is then added to the decanted mixture and agitated therein along with the sulfur. The mixture is then allowed to cool to about 60° C. and turpentine is added thereto with agitation. The final decanted mixture is then filtered through a 600 micron mesh to remove any remaining solids therefrom. The filtered liquid is cooled to ambient temperature and thereafter is ready to be used as an anorectal preparation according to this invention.

A particularly effective composition of the preparation contains ingredients in the following proportions: about 26 to 30 grams of sliced ripe berries of *Solanum carolinense* to about 250 milliliters (ml.) of triglycerides to about 5.3 grams of subliminated sulfur to about 4.4 grams of aluminum ammonium sulfate to about 10 ml. of turpentine. It is foreseen that the proportions of various ingredients in the preparation, the compounding conditions of the preparation and particular ingredients of the preparation can be varied extensively from the above particular composition and still constitute the invention as described and claimed herein.

The examples which follow will serve to illustrate the production of several anorectal medicinal preparations according to this invention.

EXAMPLES OF THE INVENTION

Example I 250 ml. of salt pork fat was placed in a beaker and heated to 95° C. Thereafter 26 grams of sliced berries of *Solanum carolinense* were added to the beaker and agitated for one minute. Thereafter, 5.3 grams of subliminated sulfur were added to the surface of the fat and allowed to set for 30 seconds before agitating. While continuing agitation, 4.4 grams of aluminum ammonium sulfate were added to the beaker. The mixture was cooled to 60° C. and 8 ml. of turpentine was added to and agitated into the mixture. The final mixture was filtered through a 600 micron mesh to remove large solids and the filtered liquid therefrom was cooled to ambient temperature, thereby constituting a preparation according to the present invention.

Example II

In this experiment the same ingredients and compounding conditions were used as in Example I above for producing a preparation according to the present invention, except that a conventional vegetable oil mixture was used in place of salt port fat and 28 grams of the berries were used therein.

Both of the above examples produced a viscus liquid ointment. The curative effects of the ointment were demonstrated by topically applying about 5 gram portions of the preparation directly to the diseased area of sufferers of anorectol disorders or irritations. The applications were repeated usually 3 times at from 24 to 48 hour intervals, preferably after taking a hot bath or sitting in a sauna. After the 3rd application most sufferers, especially those of hemorrhoids, found themselves substantially cured with consequent cessation of pain and ease of elimination, with further applications being unnecessary.

It is to be understood that while certain embodiments of this invention have been described, the invention is not to be limited to the specific forms and examples described herein.

Having thus described the invention, what is claimed and desired to secure by Letters Patent is:

1. A preparation for relief of the swelling sympton of hemmorrhoids by topical application thereto, said preparation comprising:
   (a) fragments of ripe berries of the plant *Solanum carolinense;* combined with
   (b) an application medium comprising polyglycerides; said polyglycerides being compatible for use with human tissue;
   (c) in the nature of about 250 milliters of said polyglycerides being included in said preparation for each 26 to 30 grams of said berry fragments.

2. The preparation according to claim 1 including the following composition proportions for about 26 to about 30 grams of said berry fragments:
  (a) about 5.3 grams of sulfur;
  (b) about 4.4 grams of aluminum ammonium sulfate; and
  (c) about 8 milliliters of turpentine; and
  (d) wherein said polyglycerides are salt port fat.

3. A method for treating hemorrhoid swelling in a human including the step of:
  (a) applying a dosage in the nature of 5 grams of a preparation during about a 24 to 48 hour period for at least 3 consecutive such periods to the anorectal region wherein hemorrhoids are present; and wherein
  (b) said preparation comprises the following composition proportions:
    (1) from about 26 grams to about 30 grams of fragmatized ripe berries of the plant *Solanum carolinense;*
    (2) about 250 milliliters of polyglycerides compatible for use with human tissue;
    (3) about 5.3 grams of sulfur;
    (4) about 4.4 grams of aluminum ammonium sulfate; and
    (5) about 8 milliliters of turpentine.

* * * * *